US005958972A

United States Patent [19]

Hupe et al.

[11] Patent Number: 5,958,972

[45] Date of Patent: Sep. 28, 1999

[54] TRICYCLIC INHIBITORS OF MATRIX METALLOPROTEINASES

[75] Inventors: Donald Hupe; Linda Lea Johnson, both of Ann Arbor; Joseph Armand Picard, Canton; Andrew David White, Lakeland; Qi-Zhuang Ye, Ann Arbor, all of Mich.

[73] Assignee: Warner-Lambert Company, Morris Plains, N.J.

[21] Appl. No.: 08/859,437

[22] Filed: May 20, 1997

Related U.S. Application Data

[62] Division of application No. 08/460,436, Jun. 2, 1995, Pat. No. 5,665,764.

[51] Int. Cl.$^6$ .......................... A61K 31/215; A61K 31/44
[52] U.S. Cl. .......................... 514/529; 514/290; 514/292; 514/577; 562/466; 560/56; 560/55; 546/85; 546/86; 546/87; 546/111
[58] Field of Search .................................. 514/529, 577, 514/290, 292; 560/56, 55; 562/466; 546/85, 86, 87, 111

[56] References Cited

U.S. PATENT DOCUMENTS

| 3,649,651 | 3/1972 | Dobson | 260/346.2 |
|---|---|---|---|
| 3,728,349 | 4/1973 | Dobson et al. | 424/285 |
| 5,326,760 | 7/1994 | McElroy et al. | 514/235.2 |

OTHER PUBLICATIONS

Dygos, J.H., et al., *J of Med Chem*, 1977, 20:12, 1705–1708.
Campaigne, E., et al., *J Hetero Chem*, 1969, 6:6, 885–889.
Child, et al., Arzneim–Forsch/*Drug Res*, 1980, 30(I):4a, 695–702.
International Search Report.
Mather, K C et al CA97:55445 (1981).
CA 55: 10405 a.
*Brain*, vol. 111, 1988, Miller et al., pp. 927–939.
*Neurology*, vol. 41, 1991, Barkhof et al., pp. 1219–1222.
*Biochemical Pharmacology*, vol. 47, No. 10, 1994, Moor et al., pp. 1717–1724.
*Nature*, vol. 356, 1992, Yednock et al., pp. 63–66.
*Brain Research*, vol. 576, 1992, Rosenberg et al., pp. 203–207.
*J. Cell Biology*, vol. 125, No. 5, 1994, Romanic and Madri, pp. 1165–1178.
*TiPS Reviews*, vol. 14, 1993, Dijkstra et al., pp. 124–129.
*Annals of Neurology*, vol. 36, 1994, Wekerle et al., pp. S47–S53.
*J. Neurochem.*, vol. 50, No. 3, 1988, Chantry et al., pp. 688–694.
*Biochemical and Biophysical Research Communications*, vol. 192, No. 3, 1993, Proost et al., pp. 1175–1181.
*Journal of Cellular Physiology*, vol. 157, 1993, Weeks et al., pp. 644–649.
*Biochemica et Biophysica Acta*, vol. 1176, 1993, Montgomery et al., pp. 265–268.
*Current Opinion in Neurology and Neurosurgery*, vol. 5, 1992, Lublin, pp. 182–187.

*Journal of Neuroimmunology*, vol. 21, 1989, Sternberger et al., pp. 241–248.
*Nature*, vol. 370, 1994, Mohler et al., pp. 218–220.
*Nature*, vol. 370, 1994, Gearing et al., pp. 555–557.
*The Journal of Immunology*, vol. 154, 1995, Verbeek et al., pp. 5876–5884.
*Cellular Immunology*, vol. 81, 1983, McKenna et al., pp. 391–402.
*Cellular Immunology*, vol. 112, 1988, Bitar and Whitacre, pp. 364–370.
*Journal of Neuroimmunology*, vol. 34, 1991, Kuroda and Shimamoto, pp. 159–164.
*The Journal of Immunology*, vol. 147, No. 7, 1991, Whitacre et al., pp. 2155–2163.
*Journal of Neuroimmunology*, vol. 38, 1992, O'Neill et al., pp. 53–62.
*Journal of Neuroimmunology*, vol. 39, 1992, Whitacre et al., pp. 175–182.
*Cellular and Molecular Immunology*, ed. Saunders, 1991, Abbas et al., pp. 364–369.
*Nature*, vol. 370, 1994, McGeehan et al., pp. 558–561.
*J. Clin. Invest.*, vol. 94, 1994, Galis et al., pp. 2494–2503.
*Proc. Nat'l. Acad. Sci. USA*, vol. 88, 1991, Henney et al., pp. 8154–8158.
*Clin. Sci.*, vol. 81, 1991, Vine and Powell, pp. 233–239.
*Am. J. Cardiol.*, vol. 72, 1993, Lee et al., pp. 672–676.
*Clin. Res.*, vol. 41, 1993, Reddy et al., p. 660A.
*Clin. Res.*, vol. 41, 1993, Tyagi et al., p. 681A.
*Can. J. Cardiol.*, vol. 10, 1994, Armstrong et al., pp. 214–220.
*Am. J. Physiol.*, vol. 263, 1992, Sabbah et al., pp. H266–H270.
*Circulation Research*, vol. 75, 1994, Bendeck et al., pp. 539–545.
*Circulation Research*, vol. 75, 1994, Pauly et al., pp. 41–54.
*J. Periodontal Res.*, vol. 16, 1981, Uitto et al., pp. 417–424.
*J. Periodontal Res.*, vol. 22, 1987, Overall et al., pp. 81–88.
*Arch. Opthalmol.*, vol. 81, 1969, Brown et al., pp. 370–373.
*Invest. Opththamol.*, vol. 30, 1989, Burns et al., pp. 1569–1575.
*Cancer Res.*, vol. 53, 1993, Davies et al., pp. 2087–2091.
*Cancer Res.*, vol. 52, 1992, Melchiori et al., pp. 2353–2356.
*Cancer Res.*, vol. 52, 1992, DeClerck et al., pp. 701–708.

(List continued on next page.)

*Primary Examiner*—Amelia Owens
*Attorney, Agent, or Firm*—Francis J. Tinney

[57] ABSTRACT

Tricyclic compounds are described as well as methods for the preparation and pharmaceutical compositions of same, which are useful as inhibitors of matrix metalloproteinases, particularly gelatinase A (72 kD gelatinase) and stromelysin-1 and for the treatment of multiple sclerosis, atherosclerotic plaque rupture, aortic aneurism, heart failure, restenosis, periodontal disease, corneal ulceration, cancer metastasis, tumor angiogenesis, arthritis, or other autoimmune or inflammatory disorders dependent upon tissue invasion by leukocytes.

16 Claims, No Drawings

OTHER PUBLICATIONS

*J. Biol. Chem.,* vol. 268, No. 19, 1993, Strongin et al., pp. 14033–14039.

*Cancer Res.,* vol. 53, 1993, Monsky et al., pp. 3159–3164.

*Journal of the National Cancer Institute,* vol. 87, No. 4, 1995, Taraboletti et al., pp. 293–298.

*Oncology Research,* vol. 6, 1994, Benelli et al., pp. 251–257.

*Arthritis and Rheumatism,* vol. 35, No. 1, 1992, Walakovits et al., pp. 35–42.

*J. Rheumatol.,* vol. 20, No. 4, 1993, Zafarullah et al., pp. 693–697.

*Agents Actions,* vol. 37, No. 1/2, 1992, Andrews et al., pp. 147–154.

*Biochem. Biophys. Res. Commun.,* vol. 201, No. 1, 1994, Ellis et al., pp. 94–101.

*J. Clin. Invest.,* vol. 94, 1994, Gijbels et al., pp. 2177–2182.

*Scientific American,* vol. 269, No. 3, 1993, Steinman, pp. 107–114.

*Cell–Immunol.,* vol. 82, No. 1, 1983, Paterson, pp. 55–74.

*Annals of the New York Academy of Sciences,* eds Scheinberg and Raine, vol. 436, 1984, Bornstein et al., pp. 366–372.

*Bio/technology,* vol. 13, 1995, Steinman and Conlon, pp. 118–120.

*Immunol–Ser.,* vol. 59, 1993, Steinman et al., pp. 253–260.

*The Blood Brain Barrier in Health and Disease,* edited by Suckling et al., 1986, Lam, pp. 158–164.

TRICYCLIC INHIBITORS OF MATRIX METALLOPROTEINASES

This application is a division of application Ser. No. 08/460,436 filed Jun. 2, 1995 which application is now U.S. Pat. No. 5,665,764.

BACKGROUND OF THE INVENTION

The present invention relates to novel tricyclic compounds useful as pharmaceutical agents, to methods for their production, to pharmaceutical compositions which include these compounds and a pharmaceutically acceptable carrier, and to pharmaceutical methods of treatment. The novel compounds of the present invention are inhibitors of matrix metalloproteinases, e.g., gelatinase A (72 kDa gelatinase) and stromelysin-1. More particularly, the novel compounds of the present invention are useful in the treatment of atherosclerotic plaque rupture, aortic aneurism, heart failure, restenosis, periodontal disease, corneal ulceration, cancer metastasis, tumor angiogenesis, arthritis, multiple sclerosis, and other autoimmune or inflammatory disorders dependent on the tissue invasion of leukocytes or other activated migrating cells.

Gelatinase A and stromelysin-1 are members of the matrix metalloproteinase (MMP) family (Woessner J. F., *FASEB J.* 1991;5:2145–2154). Other members include fibroblast collagenase, neutrophil collagenase, gelatinase B (92 kDa gelatinase), stromelysin-2, stromelysin-3, matrilysin, collagenase 3 (Freije J. M., Diez-Itza I., Balbin M., Sanchez L. M., Blasco R., Tolivia J., and Lopez-Otin C. *J. Biol. Chem.,* 1994;269:16766–16773), and the newly discovered membrane-associated matrix metalloproteinases (Sato H., Takino T., Okada Y., Cao J., Shinagawa A., Yamamoto E., and Seiki M., *Nature,* 1994;370:61–65).

Matrix metalloproteinases share high sequence homology and the catalytic domains of each of the MMPs can be identified by sequence alignment. The gene for the catalytic domain of stromelysin-1, SCD, was constructed by removing the propeptide and C-terminal domain (Ye Q. -Z., Johnson L. L, Hupe D. J., and Baragi V., "Purification and Characterization of the Human Stromelysin Catalytic Domain Expressed in *Escherichia coli*", *Biochemistry,* 1992;31:11231–11235). The gelatinase A catalytic domain, GCD, was similarly constructed with the additional removal of the fibronectin-like insert which interrupts the catalytic domain (Ye Q. -Z., Johnson L. L, Yu A. E., and Hupe D., "Reconstructed 19 kDa Catalytic Domain of Gelatinase A is an Active Proteinase", *Biochemistry,* 1995;34:4702–4708). Both truncated proteins cleave synthetic peptide substrates and the natural substrates proteoglycan and gelatin in a manner similar to the full-length enzymes and can be used to identify matrix metalloproteinase inhibitors.

The catalytic zinc in matrix metalloproteinases is the focal point for inhibitor design. The modification of substrates by introducing chelating groups has generated potent inhibitors such as peptide hydroxymates, thio-containing peptides, and N-carboxyalkyl peptides. Peptide hydroxymates and the natural endogenous inhibitors of MMPs (TIMPs) have been used successfully to treat animal models of cancer and inflammation. However, except for amino acid derivatives with weak potency (Ye Q. -Z., Johnson L. L., Nordan I., Hupe D., and Hupe L.,*J. Med. Chem.* 1994;37(1):206–209), few non-peptide inhibitors have been described and shown to have in vivo activity.

The ability of the matrix metalloproteinases to degrade various components of connective tissue makes them potential targets for controlling pathological processes. For example, the rupture of atherosclerotic plaques is the most common event initiating coronary thrombosis. Destabilization and degradation of the extracellular matrix surrounding these plaques by MMPs has been proposed as a cause of plaque fissuring. The shoulders and regions of foam cell accumulation in human atherosclerotic plaques show locally increased expression of gelatinase B, stromelysin-1, and interstitial collagenase. In situ zymography of this tissue revealed increased gelatinolytic and caseinolytic activity (Galla Z. S., Sukhova G. K., Lark M. W., and Libby P., "Increased expression of matrix metalloproteinases and matrix degrading activity in vulnerable regions of human atherosclerotic plaques", *J. Clin. Invest.,* 1994;94:2494–2503). In addition, high levels of stromelysin RNA message have been found to be localized to individual cells in atherosclerotic plaques removed from heart transplant patients at the time of surgery (Henney A. M., Wakeley P. R., Davies M. J., Foster K., Hembry R., Murphy G., and Humphries S., "Localization of stromelysin gene expression in atherosclerotic plaques by in situ hybridization", *Proc. Nat'l. Acad. Sci.* 1991;88:8154–8158).

Inhibitors of matrix metalloproteinases will have utility in treating degenerative aortic disease associated with thinning of the medial aortic wall. Increased levels of the proteolytic activities of MMPs have been identified in patients with aortic aneurisms and aortic stenosis (Vine N. and Powell J. T., "Metalloproteinases in degenerative aortic diseases", *Clin. Sci.,* 1991;81:233–239).

Heart failure arises from a variety of diverse etiologies, but a common characteristic is cardiac dilation which has been identified as an independent risk factor for mortality (Lee T. H., Hamilton M. A., Stevenson L. W., Moriguchi J. D., Fonarow G. C., Child J. S., Laks H., and Walden J. A., "Impact of left ventricular size on the survival in advanced heart failure", *Am. J. Cardiol.,* 1993;72:672–676). This remodeling of the failing heart appears to involve the breakdown of extracellular matrix. Matrix metalloproteinases are increased in patients with both idiopathic and ischemic heart failure (Reddy H. K., Tyagi S. C., Tjaha I. E., Voelker D. J., Campbell S. E., Weber K. T., "Activated myocardial collagenase in idiopathic dilated cardiomyopathy", *Clin. Res.,* 1993;41:660A; Tyagi S. C., Reddy H. K., Voelker D., Tjara I. E., Weber K. T., "Myocardial collagenase in failing human heart", *Clin. Res.,* 1993;41:681A). Animal models of heart failure have shown that the induction of gelatinase is important in cardiac dilation (Armstrong P. W., Moe G. W., Howard R. J., Grima E. A., Cruz T. F., "Structural remodeling in heart failure: gelatinase induction", *Can. J. Cardiol.,* 1994;10:214–220), and cardiac dilation precedes profound deficits in cardiac function (Sabbah H. N., Kono T., Stein P. D., Mancini G. B., Goldstein S., "Left ventricular shape changes during the course of evolving heart failure", *Am. J. Physiol.,* 1992;263:H266–H270).

Neointimal proliferation, leading to restenosis, frequently develops after coronary angioplasty. The migration of vascular smooth muscle cells (VSMCs) from the tunica media to the neointima is a key event in the development and progression of many vascular diseases and a highly predictable consequence of mechanical injury to the blood vessel (Bendeck M. P., Zempo N., Clowes A. W., Galardy R. E., Reidy M., "Smooth muscle cell migration and matrix metalloproteinase expression after arterial injury in the rat", *Circulation Research,* 1994;75:539–545). Northern blotting and zymographic analyses indicated that gelatinase A was the principal MMP expressed and excreted by these cells.

Further, antisera capable of selectively neutralizing gelatinase A activity also inhibited VSMC migration across basement membrane barrier. After injury to the vessel, gelatinase A activity increased more than 20-fold as VSCMs underwent the transition from a quiescent state to a proliferating, motile phenotype (Pauly R. R., Passaniti A., Bilato C., Monticone R., Cheng L., Papadopoulos N., Gluzband Y. A., Smith L., Weinstein C., Lakatta E., Crow M. T., "Migration of cultured vascular smooth muscle cells through a basement membrane barrier requires type IV collagenase activity and is inhibited by cellular differentiation", *Circulation Research,* 1994;75:41–54).

Collagenase and stromelysin activities have been demonstrated in fibroblasts isolated from inflamed gingiva (Uitto V. J., Applegren R., Robinson P. J., "Collagenase and neutral metalloproteinase activity in extracts from inflamed human gingiva", *J. Periodontal Res.,* 1981;16:417–424), and enzyme levels have been correlated to the severity of gum disease (Overall C. M., Wiebkin O. W., Thonard J. C., "Demonstrations of tissue collagenase activity in vivo and its relationship to inflammation severity in human gingiva", *J. Periodontal Res.,* 1987;22:81–88). Proteolytic degradation of extracellular matrix has been observed in corneal ulceration following alkali burns (Brown S. I., Weller C. A., Wasserman H. E., "Collagenolytic activity of alkali burned corneas", *Arch. Opthalmol.,* 1969;81:370–373). Thio-containing peptides inhibit the collagenase isolated from alkali-burned rabbit corneas (Burns F. R., Stack M. S., Gray R. D., Paterson C. A., *Invest. Opththamol.,* 1989;30:1569–1575).

Davies, et al. (*Cancer Res.,* 1993;53:2087–2091) reported that a peptide hydroxymate, BB-94, decreased the tumor burden and prolonged the survival of mice bearing human ovarian carcinoma xenografts. A peptide of the conserved MMP propeptide sequence was a weak inhibitor of gelatinase A and inhibited human tumor cell invasion through a layer of reconstituted basement membrane (Melchiori A., Albili A., Ray J. M., and Stetler-Stevenson W. G., *Cancer Res.,* 1992;52:2353–2356), and the natural tissue inhibitor of metalloproteinase-2 (TIMP-2) also showed blockage of tumor cell invasion in in vitro models (DeClerck Y. A., Perez N., Shimada H., Boone T. C., Langley K. E., and Taylor S. M., *Cancer Res.,* 1992;52:701–708). Studies of human cancers have shown that gelatinase A is activated on the invasive tumor cell surface (A. Y. Strongin, B. L. Marmer, G. A. Grant, and G. I. Goldberg, *J. Biol Chem.,* 1993;268:14033–14039) and is retained there through interaction with a receptor-like molecule (Monsky W. L., Kelly T., Lin C. -Y., Yeh Y., Stetler-Stevenson W. G., Mueller S. C., and Chen W. -T., *Cancer Res.,* 1993;53:3159–3164).

Inhibitors of MMPs have shown activity in models of tumor angiogenesis (Taraboletti G., Garofalo A., Belotti D., Drudis T., Borsotti P., Scanziani E., Brown P. D., and Giavazzi R., *Journal of the National Cancer Institute,* 1995;87:293 and Benelli R., Adatia R., Ensoli B., Stetler-Stevenson W. G., Santi L., and Albini A, *Oncology Research,* 1994;6:251–257).

Several investigators have demonstrated consistent elevation of stromelysin and collagenase in synovial fluids from rheumatoid and osteoarthritis patients as compared to controls (Walakovits L. A., Moore V. L., Bhardwaj N., Gallick G. S., and Lark M. W., "Detection of stromelysin and collagenase in synovial fluid from patients with rheumatoid arthritis and posttraumatic knee injury", *Arthritis Rheum.,* 1992;35:35–42; Zafarullah M., Pelletier J. P., Cloutier J. M., and Marcel-Pelletier J., "Elevated metalloproteinases and tissue inhibitor of metalloproteinase mRNA in human osteoarthritic synovia", *J. Rheumatol.,* 1993;20:693–697). TIMP-1 and TIMP-2 prevented the formation of collagen fragments, but not proteoglycan fragments, from the degradation of both the bovine nasal and pig articular cartilage models for arthritis, while a synthetic peptide hydroxymate could prevent the formation of both fragments (Andrews H. J., Plumpton T. A., Harper G. P., and Cawston T. E., *Agents Actions,* 1992;37:147–154; Ellis A. J., Curry V. A., Powell E. K., and Cawston T. E., *Biochem. Biophys. Res. Commun.,* 1994;201:94–101).

Gijbels, et al., (*J. Clin. Invest.* 1994;94:2177–2182) recently described a peptide hydroxymate, GM6001, that suppressed the development or reversed the clinical expression of experimental allergic encephalomyelitis (EAE) in a dose dependent manner, suggesting the use of MMP inhibitors in the treatment of autoimmune inflammatory disorders such as multiple sclerosis.

Multiple sclerosis (MS) is a complex demyelinating disease of the central nervous system (CNS) characterized by inflammation, disruption of the blood-brain barrier, selective destruction of the myelin sheaths with glial scar formation and loss of neuronal cell conductivity leading to neurological deficits. The underlying cause is unknown, but it has been established as a T-cell mediated autoimmune disease (Lawrence Steinman, "Autoimmune Disease", *Scientific American,* September 1993;269(3):106–114). While there are no spontaneous animal models for the disease, experimental allergic encephalomyelitis (EAE) has been used successfully to study many aspects of MS pathogenesis, and the work of Paterson and others has clearly and convincingly demonstrated the validity of this model as the only accepted preclinical test for efficacy of agents in MS (Paterson P., "Going to the Rats and Dogs to Study the Patient," *Cell-Immunol.,* 1983;82(1):55–74). Bornstein's work using mammalian organotypic cultures showed that the CNS tissue responded with identical patterns of demyelination, swollen myelin sheaths, and eventual "sclerosis" when exposed to serum from EAE-affected animals and MS patients (Bornstein M. B., Miller A. I., Slagle S., Arnon R., Sela M., and Teitelbaum D., "Clinical Trials of Copolymer I in Multiple Sclerosis," in *Annals of the New York Academy of Sciences,* eds Labe Scheinberg and Cedric S. Raine, 1984;36:366–372). Analysis of the receptors on T-cells isolated from brain lesions of MS patients reveal that they are reactive to a peptide fragment of myelin basic protein analogous to the antigen used to precipitate the EAE model (Lawrence Steinman and Paul Conlon, "Designing rational therapies for multiple sclerosis," *Bio/technology,* February 1995:118–120).

Several successful therapeutic strategies for treating MS target the T-cell response modeled in EAE. Beta-interferon (betaseron), acts in part by downregulating the expression of histocompatibility locus antigen (HLA) DR2. EAE studies have been used as the primary experimental basis to develop many of the current treatments for MS. Copolymer-1 and oral administration of myelin basic protein act by inducing immune tolerance to the myelin basic protein (MBP) antigen. The EAE model was used to develop a therapy in which peptides derived from the T-cell receptor V region recognizing an MBP fragment are used to immunize patients with relapsing-remitting MS. Monoclonal antibodies (Mab) against the CD4 receptor prevented the clinical and histological manifestations of EAE (Steinman L., Lindsey J. W., Alters S., and Hodgkinson S., "From treatment of experimental allergic encephalomyelitis to clinical trials in multiple sclerosis," *Immunol-Ser.,* 1993;59:253–60). Clinical trials of CD4 Mabs are being conducted by several companies.

In MS and EAE, the blood-brain barrier has been shown to be defective both with respect to exclusion of blood-borne substances from the CNS and infiltration of lymphocytes (Lam D. K. C., "The central nervous system barrier in acute experimental allergic encephalomyelitis," in *The Blood Brain Barrier in Health and Disease,* edited by Suckling A. J., Rumsby M. G., and Bradbury M. W. B., 1986:158–164, Ellis Horwood, Ltd., Chichester, UK). Using gadolinium-DTPA enhanced magnetic resonance imaging (MRI), Miller, et al. (Miller D. H., Rudge P., Johnson G., Kendall B. E., MacManus D. G., Moseley I. F., Barnes D., and McDonald W. I., "Serial gadolinium enhanced magnetic resonance imaging in multiple sclerosis," *Brain,* 1988;111:927–939) showed in a serial study of MS patients that in recognizable new lesions or in new parts of existing lesions, blood-brain barrier impairment was always present. It appears that blood-brain barrier disruption is the beginning of an irreversible cascade of events leading to demyelination (Barkhof F., Hommes O. R., Scheltens P., and Valk J., "Quantitative MRI changes in gadolinium-DPTA enhancement after high-dose intravenous methyl-prednisolone in multiple sclerosis," *Neurology,* 1991;14:1219–1222) and is necessary for the development of the disease (Moor A. C. E., De Vries H. E., De Boer A. G., and Breimer D. D., *Biochemical Pharmacology,* 1994;47:1717–1724). Previously, it has been shown that neutralizing antibodies to cell adhesion molecules prevent lymphocyte infiltration in the EAE, and that this inhibits the inflammatory response initiating the encephalomyelitis (Yednock T. A., Cannon C., Fritz L. C., Sanchez-Madrid F., Steinman L., and Karin N., "Prevention of experimental autoimmune encephalomyelitis by antibodies against α4 β1 integrin," *Nature,* Mar. 5, 1992;356(6364):63–66). It has therefore been predicted that agents that prevent such infiltration may be among the most inviting prospects for therapy in MS.

The mechanism through which the blood-brain barrier is disrupted during the pathogenesis of MS and other inflammatory diseases of the central nervous system is under intense study. Rosenberg, et al. showed that activated gelatinase A injected intracerebrally attacks extracellular matrix and opens the blood-brain barrier. Treatment with TIMP-2 reduced the proteolysis and protected the blood-brain barrier. (Rosenberg G. A., Kornfeld M., Estrada E., Kelley R. O., Liotta L., and Stetler-Stevenson W. G., "TIMP-2 reduces proteolytic opening of the blood-brain barrier by type IV collagenase", *Brain Research,* 1992;576:203–207). A recent study by Madri has elucidated the role of gelatinase A in the extravasation of T-cells from the blood stream during inflammation (Ramanic A. M., and Madri J. A., "The Induction of 72-kD Gelatinase in T Cells upon Adhesion to Endothelial Cells is VCAM-1 Dependent", *J. Cell Biology,* 1994;125:1165–1178). This transmigration past the endothelial cell layer is coordinated with the induction of gelatinase A and is mediated by binding to the vascular cell adhesion molecule-1 (VCAM-1). Once the barrier is compromised, edema and inflammation are produced in the CNS. Leukocytic migration across the blood-brain barrier is known to be associated with the inflammatory response in EAE. Inhibition of the metalloproteinase gelatinase A would block the degradation of extracellular matrix by activated T-cells that is necessary for CNS penetration.

These studies provide the basis for the expectation that an effective, bioavailable inhibitor of gelatinase A and/or stromelysin-1 would have value in the treatment of diseases involving disruption of extracellular matrix resulting in inflammation due to lymphocytic infiltration, inappropriate migration of metastatic or activated cells, or loss of structural integrity necessary for organ function.

We have identified a series of tricyclic compounds that are inhibitors of matrix metalloproteinases, particularly gelatinase A and stromelysin-1, and are additionally active in an allergic encephalomyelitis model and thus useful as agents for the treatment of multiple sclerosis, atherosclerotic plaque rupture, restenosis, aortic aneurism, heart failure, periodontal disease, corneal ulceration, cancer metastasis, tumor angiogenesis, arthritis, or other autoimmune or inflammatory diseases dependent upon tissue invasion by leukocytes.

SUMMARY OF THE INVENTION

Accordingly, the present invention is a compound of Formula I

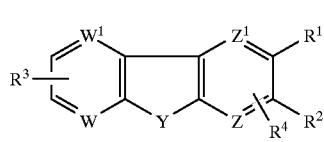

wherein one of $R^1$ or $R^2$ is

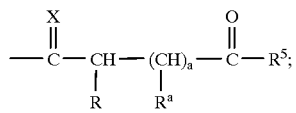

wherein X is O,

N—$OR^6$ wherein $R^6$ is hydrogen,
—$(CH_2)_n$-aryl wherein n is zero or an integer of 1 to 5, alkyl, or
—$(CH_2)_n$-cycloalkyl wherein n is as defined above, or

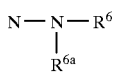

wherein $R^6$ and $R^{6a}$ are each the same or different and each is as defined above for $R^6$;

R and $R^a$ are each the same or different and each is hydrogen,
—$(CH_2)_n$-aryl wherein n is as defined above,
—$(CH_2)_n$-heteroaryl wherein n is as defined above,
—$(CH_2)_p$—$R^7$—$(CH_2)_q$-aryl wherein $R^7$ is O or S and p or q is each zero or an integer of 1 to 5 and the sum of p+q is not greater than an integer of 5,
—$(CH_2)_p$—$R^7$—$(CH_2)_q$-heteroaryl wherein p, q, and $R^7$ are as defined above,
alkyl,
—$(CH_2)_n$-cycloalkyl wherein n is as defined above, or
—$(CH_2)_r$—$NH_2$ wherein r is an integer of 1 to 9;
a is zero or an integer of 1 to 3;
$R^5$ is OH,
$OR^6$ wherein $R^6$ is as defined above,

wherein $R^6$ and $R^{6a}$ are each the same or different and are as defined above for $R^6$, or
NH—$OR^6$ wherein $R^6$ is as defined above;

$R^3$ and $R^4$ are each the same or different and each is hydrogen, alkyl, $NO_2$, halogen, $OR^6$ wherein $R^6$ is as defined above,

CN, $CO_2R^6$ wherein $R^6$ is as defined above, $SO_3R^6$ wherein $R^6$ is as defined above,

CHO,

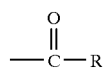

wherein R is as defined above,

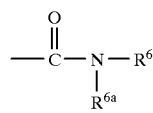

wherein $R^6$ and $R^{6a}$ are each the same or different and are as defined above for $R^6$, or

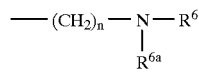

wherein $R^6$ and $R^{6a}$ are each the same or different and are as defined above for $R^6$;

W, $W^1$, Z, and $Z^1$ are each the same or different and each is $CR^3$ wherein $R^3$ is as defined above, or N providing only one of W or $W^1$ is N and/or only one of Z or $Z^1$ is N; and Y is

wherein R is as defined above,

—O—,

—S—$(O)_m$—wherein m is zero or an integer of 1 or 2,

—$CH_2$—,

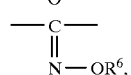

wherein $R^6$ is as defined above,

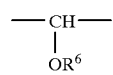

wherein $R^6$ is as defined above,

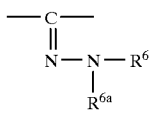

wherein $R^6$ and $R^{6a}$ are the same or different and are as defined above for $R^6$,

wherein $R^6$ is as defined above,

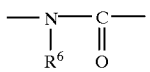

wherein $R^6$ is as defined above,

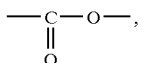

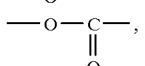

—$CH_2$—O—,

—O—$CH_2$—,

—$CH_2$—$S(O)_m$— wherein m is as defined above,

—$S(O)_m$—$CH_2$— wherein m is as defined above,

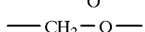

wherein $R^6$ is as defined above,

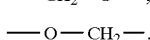

wherein $R^6$ is as defined above,

—CH=N—, or

—N=CH—;

with the proviso that when X is O, and $R^5$ is not NH—$OR^6$, at least one of R or $R^a$ is not hydrogen; and corresponding isomers thereof; or a pharmaceutically acceptable salt thereof.

As matrix metalloproteinase inhibitors, the compounds of Formula I are useful as agents for the treatment of MS. They are also useful as agents for the treatment of atherosclerotic plaque rupture, restenosis, periodontal disease, corneal ulceration, cancer metastasis, tumor angiogenesis, arthritis, and other inflammatory disorders dependent upon tissue invasion by leukocytes.

A still further embodiment of the present invention is a pharmaceutical composition for administering an effective amount of a compound of Formula I in unit dosage form in the treatment methods mentioned above. Finally, the present invention is directed to methods for production of compounds of Formula I.

DETAILED DESCRIPTION OF THE INVENTION

In the compounds of Formula I, the term "alkyl" means a straight or branched hydrocarbon radical having from 1 to 8 carbon atoms and includes, for example, methyl, ethyl, n-propyl, isopropyl, n-butyl, sec-butyl, isobutyl, tert-butyl, n-pentyl, n-hexyl, n-heptyl, n-octyl, and the like.

"Alkoxy" and "thioalkoxy" are O-alkyl or S-alkyl of from 1 to 6 carbon atoms as defined above for "alkyl".

The term "cycloalkyl" means a saturated hydrocarbon ring having 3 to 8 carbon atoms and includes, for example, cyclopropyl, cyclobutyl, cyclopentyl, cyclohexyl, cycloheptyl, cyclooctyl, and the like.

The term "aryl" means an aromatic radical which is a phenyl group, a phenyl group substituted by 1 to 4 substituents selected from alkyl as defined above, alkoxy as defined above, thioalkoxy as defined above, hydroxy, halogen, trifluoromethyl, amino, alkylamino as defined above for alkyl, dialkylamino as defined for alkyl, nitro, cyano, carboxy, $SO_3H$, CHO,

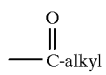

as defined above for alkyl,

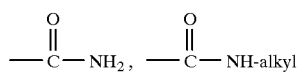

as defined above for alkyl,

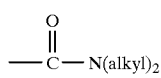

as defined above for alkyl, —$(CH_2)_n2$—$NH_2$ wherein $n^2$ is an integer of 1 to 5, —$(CH_2)_n2$—NH-alkyl as defined above for alkyl and $n^2$, —$(CH_2)_n2$—$N(alkyl)_2$ as defined above for alkyl and $n^2$.

The term "heteroaryl" means a heteroaromatic radical and includes, for example, which is 2- or 3-thienyl, 2- or 3-furanyl, 2- or 3-pyrrolyl, 2-, 3-, or 4-pyridinyl, 2-pyrazinyl, 2-, 4-, or 5-pyrimidinyl, 3- or 4-pyridazinyl, or 2-, 3-, 4-, 5-, 6-, or 7-indolyl.

"Halogen" is fluorine, chlorine, bromine, or iodine.

Phenyl is abbreviated "Ph".

Some of the compounds of Formula I are capable of further forming both pharmaceutically acceptable acid addition and/or base salts. All of these forms are within the scope of the present invention.

Pharmaceutically acceptable acid addition salts of the compounds of Formula I include salts derived from nontoxic inorganic acids such as hydrochloric, nitric, phosphoric, sulfuric, hydrobromic, hydriodic, hydrofluoric, phosphorous, and the like, as well as the salts derived from nontoxic organic acids, such as aliphatic mono- and dicarboxylic acids, phenyl-substituted alkanoic acids, hydroxy alkanoic acids, alkanedioic acids, aromatic acids, aliphatic and aromatic sulfonic acids, etc. Such salts thus include sulfate, pyrosulfate, bisulfate, sulfite, bisulfite, nitrate, phosphate, monohydrogenphosphate, dihydrogenphosphate, metaphosphate, pyrophosphate, chloride, bromide, iodide, acetate, trifluoroacetate, propionate, caprylate, isobutyrate, oxalate, malonate, succinate, suberate, sebacate, fumarate, maleate, mandelate, benzoate, chlorobenzoate, methylbenzoate, dinitrobenzoate, phthalate, benzenesulfonate, toluenesulfonate, phenylacetate, citrate, lactate, maleate, tartrate, methanesulfonate, and the like. Also contemplated are salts of amino acids such as arginate and the like and gluconate, galacturonate (see, for example, Berge S. M., et al, "Pharmaceutical Salts," *J. of Pharma Sci.*, 1977;66:1.

The acid addition salts of said basic compounds are prepared by contacting the free base form with a sufficient amount of the desired acid to produce the salt in the conventional manner. The free base form may be regenerated by contacting the salt form with a base and isolating the free base in the conventional manner. The free base forms differ from their respective salt forms somewhat in certain physical properties such as solubility in polar solvents, but otherwise the salts are equivalent to their respective free base for purposes of the present invention.

Pharmaceutically acceptable base addition salts are formed with metals or amines, such as alkali and alkaline earth metals or organic amines. Examples of metals used as cations are sodium, potassium, magnesium, calcium, and the like. Examples of suitable amines are N,N'-dibenzylethylenediamine, chloro-procaine, choline, diethanolamine, dicyclohexylamine, ethylenediamine, N-methylglucamine, and procaine (see, for example, Berge S. M., et al., "Pharmaceutical Salts," *J. of Pharma Sci.*, 1977;66:1.

The base addition salts of said acidic compounds are prepared by contacting the free acid form with a sufficient amount of the desired base to produce the salt in the conventional manner. The free acid form may be regenerated by contacting the salt form with an acid and isolating the free acid in the conventional manner. The free acid forms differ from their respective salt forms somewhat in certain physical properties such as solubility in polar solvents, but otherwise the salts are equivalent to their respective free acid for purposes of the present invention.

Certain of the compounds of the present invention can exist in unsolvated forms as well as solvated forms, including hydrated forms. In general, the solvated forms, including hydrated forms, are equivalent to unsolvated forms and are intended to be encompassed within the scope of the present invention.

Certain of the compounds of the present invention possess one or more chiral centers and each center may exist in the R(D) or S(L) configuration. The present invention includes all diastereomeric, enantiomeric, and epimeric forms as well as the appropriate mixtures thereof. Additionally, the compounds of the present invention may exist as geometric isomers. The present invention includes all cis, trans, syn, anti, entgegen (E), and zusammen (Z) isomers as well as the appropriate mixtures thereof.

In one embodiment of the invention, a preferred compound of Formula I is one wherein W, $W^1$, Z, and $Z^1$ are $CR^3$; and corresponding isomers thereof; or a pharmaceutically acceptable salt thereof.

Another preferred compound of Formula I of this embodiment is one wherein

Y is

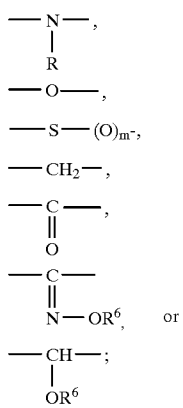

and corresponding isomers thereof;
or pharmaceutically acceptable salt thereof.

Another preferred compound of Formula I of this embodiment is one wherein one of R or R$^a$ is other than hydrogen; and corresponding isomers thereof; or a pharmaceutically acceptable salt thereof.

Another preferred compound of Formula I of this embodiment is one wherein X is N—OR$^6$; and corresponding isomers thereof; or a pharmaceutically acceptable salt thereof.

Another preferred compound of Formula I of this embodiment is one wherein R$^5$ is OH; and corresponding isomers thereof; or a pharmaceutically acceptable salt thereof.

Another preferred compound of Formula I of this embodiment is one wherein Y is —O—; and corresponding isomers thereof; or a pharmaceutically acceptable salt thereof.

Another preferred compound of Formula I of this embodiment is one wherein X is N—OH; Y is —O—; and R$^3$ and R$^4$ are each hydrogen; and corresponding isomers thereof; or a pharmaceutically acceptable salt thereof.

Another preferred compound of Formula I of this embodiment is one wherein X is O and R$^5$ is NH—OR$^6$; and corresponding isomers thereof; or a pharmaceutically acceptable salt thereof.

In another embodiment of the invention, a preferred compound of Formula I is one wherein W, W$^1$, Z, and Z$^1$ is N providing only one of W or W$^1$ is N and/or only one of Z or Z$^1$ is N; and corresponding isomers thereof; or a pharmaceutically acceptable salt, thereof.

Another preferred compound of Formula I of this embodiment is one wherein

Y is

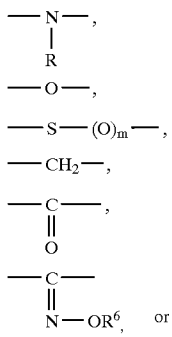

—CH—;
 |
 OR$^6$ and corresponding isomers thereof;
or a pharmaceutically acceptable salt thereof.

Another preferred compound of Formula I of this embodiment is one wherein one of R or R$^a$ is other than hydrogen; and corresponding isomers thereof; or a pharmaceutically acceptable salt thereof.

Another preferred compound of Formula I of this embodiment is one wherein X is N—OR$^6$; and corresponding isomers thereof; or a pharmaceutically acceptable salt thereof.

Another preferred compound of Formula I of this embodiment is one wherein R$^5$ is OH; and corresponding isomers thereof, or a pharmaceutically acceptable salt thereof.

Another preferred compound of Formula I of this embodiment is one wherein X is O and R$^5$ is NH—OR$^6$; and corresponding isomers thereof; or a pharmaceutically acceptable salt thereof.

Particularly valuable is a compound selected from the group consisting of:
  4-Dibenzofuran-2-yl-4-hydroxyimino-butyric acid;
  2-(2-Dibenzofuran-2-yl-2-hydroxyimino-ethyl)-4-methyl-pentanoic acid;
  2-(2-Dibenzofuran-2-yl-2-hydroxyimino-ethyl)-5-phenyl-pentanoic acid;
  4-Dibenzofuran-2-yl-4-hydroxyimino-2-phenethylbutyric acid;
  5-(4-Chloro-phenyl)-2-(2-dibenzofuran-2-yl-2-hydroxyimino-ethyl)-pentanoic acid;
  2-(2-Dibenzofuran-2-yl-2-hydroxyimino-ethyl)-5-(4-fluoro-phenyl)-pentanoic acid;
  2-(2-Dibenzofuran-2-yl-2-hydroxyimino-ethyl)-5-(4-methoxy-phenyl)-pentanoic acid;
  2-(2-Dibenzofuran-2-yl-2-hydroxyimino-ethyl)-5-p-tolyl-pentanoic acid;
  3-(Dibenzofuran-2-yl-hydroxyimino-methyl)-5-methyl-hexanoic acid;
  3-(Dibenzofuran-2-yl-hydroxyimino-methyl)-6-phenyl-hexanoic acid;
  3-(Dibenzofuran-2-yl-hydroxyimino-methyl)-5-phenyl-pentanoic acid;
  6-(4-Chloro-phenyl)-3-(dibenzofuran-2-yl-hydroxyimino-methyl)-hexanoic acid;
  3-(Dibenzofuran-2-yl-hydroxyimino-methyl)-6-(4-fluoro-phenyl)-hexanoic acid;
  3-(Dibenzofuran-2-yl-hydroxyimino-methyl)-6-(4-methoxyphenyl)-hexanoic acid; and
  3-(Dibenzofuran-2-yl-hydroxyimino-methyl)-6-p-tolyl-hexanoic acid; and
corresponding isomers thereof; or a pharmaceutically acceptable salt thereof.

More particularly valuable is 4-dibenzofuran-2-yl-4-hydroxyimino-butyric acid; and
corresponding isomers thereof; or a pharmaceutically acceptable salt thereof.

The compounds of Formula I are valuable inhibitors of gelatinase A and/or stromelysin-1. It has been shown previously that inhibitors of matrix metalloproteinases have efficacy in models of disease states like arthritis and metastasis that depend on modification of the extracellular matrix. We demonstrate here that potent and specific inhibitors of gelatinase A also have activity in the rat experimental allergic encephalomyelitis model which is predictive for human multiple sclerosis and has previously been used as a basis for predicting the efficacy of other therapeutic agents for MS, including anti-CD4 monoclonal antibody, copolymer I, betaseron, cyclosporin, and MBP oral antigen.

In vitro experiments were carried out which demonstrate the efficacy of compounds of Formula I as potent and specific inhibitors of gelatinase A and stromelysin-1, while showing lesser or no inhibition of other related matrix metalloproteinases. Experiments were carried out with both the full-length enzymes and the catalytic domains. Table I shows the activity of Example 2 versus GCD (recombinant gelatinase A catalytic domain); gelatinase A (recombinant full-length enzyme); SCD (stromelysin-1 catalytic domain); stromelysin-1 (full-length native enzyme); gelatinase B (recombinant full-length enzyme); and collagenase (full-length native enzyme). $IC_{50}$ values were determined using a thiopeptolide substrate, Ac-Pro-Leu-Gly-thioester-Leu-Leu-Gly-OEt (Ye Q. -Z., Johnson L. L., Hupe D. J., and Baragi V., "Purification and Characterization of the Human Stromelysin Catalytic Domain Expressed in *Escherichia coli*", *Biochemistry*, 1992;31:11231–11235). Example 2 inhibits the conversion of the substrate by gelatinase A with an $IC_{50}$ value of 1.31 $\mu$M. The same compound also inhibits stromelysin-1 with an $IC_{50}$ value of 7.64 $\mu$M. $IC_{50}$ values for gelatinase B, and collagenase, were >100 $\mu$M.

TABLE I

| Enzyme | Example 2 $IC_{50}$ ($\mu$M) |
| --- | --- |
| GCD | 0.040 |
| Gelatinase A | 1.31 |
| SCD | 7.12 |
| Stromelysin | 7.64 |
| Gelatinase B | >100 |
| Collagenase | >100 |

The activity of Example 2 in suppressing the inflammatory disease associated with EAE was tested using the Lewis rat acute model. Female Lewis rats were purchased from Harlan Sprague-Dawley (Indianapolis, Ind.) and were used at 8 to 10 weeks of age. Active EAE was induced by injection of 0.05 mL emulsion of myelin basic protein (MBP) with complete Freund's adjuvant (CFA), containing 25 $\mu$g guinea pig MBP and 100 $\mu$g *Mycobacterium butyricum* (Difco Laboratories, Detroit, Mich.) into one hind footpad. Immunized rats were observed daily for clinical signs of EAE and scored as follows: 0, no symptoms; 1, loss of tail tonicity; 2, paresis; 3, hind limb paralysis, often accompanied by incontinence; and 4, death. Formalin-fixed brain slice sections were stained with hematoxylin-eosin and evaluated microscopically for perivascular and parenchymal infiltration. Compound was administered by gavage as a solution in sterile saline in a volume of 500 $\mu$L. The dose of 50 mg/kg typically required 7.5 mg of compound per rat. Several different protocols were used to define the efficacy and timing requirements for potency. Three separate protocols which demonstrate efficacy are described below.

Protocol 1: Compound was administered daily at 50 mg/kg beginning on Day 0 and continuing through Day 14, with MBP in CFA administered on Day 0 also. As shown in Table II, this treatment substantially reduced the average scores for the treated group. The percentage of animals responding is also very high with 100% of treated animals showing either a total inhibition of symptoms (80%) or reduction of symptoms (20%). N=5 for all groups.

TABLE II

| Treatment | Daily Oral Dosing Begun at Day 0 | Clinical Grade at Peak of Disease | SD | Day of Peak Expression | Effect on EAE Rats (≧Paresis/ Total) |
| --- | --- | --- | --- | --- | --- |
| CFA | Phosphate-Buffered Saline (PBS) | 0 | 0 | — | 0/5 |
| CFA + Example 2 | 50 mg/kg | 0 | 0 | — | 0/5 |
| CFA + MBP | PBS | 3.0 | 0.0 | 13 & 14 | 5/5 |
| CFA + MBP + Example 2 | 50 mg/kg | 1.0 | 1.22 | 12 | 1/5 |

Protocol 2: To determine whether less frequent dosing or dosing at lower levels was still effective at suppressing EAE, compound was administered at either 50 mg/kg or at 10 mg/kg on Day 0 and on alternate days through Day 14. As shown in Table III, this protocol demonstrated a similar effect on average clinical scores at the peak of disease expression for the treatment group. The decrease in disease severity was highly significant (p≦0.01) for Day 15. Controls run in parallel included CFA only and MBP in CFA. N=4 for treatment groups. N=8 for controls.

TABLE III

| Treatment | Dosage | Clinical Grade at Peak of Disease | SD | Day of Peak Expression | Effect on EAE Rats (≧Paresis/ Total) |
| --- | --- | --- | --- | --- | --- |
| CFA | PBS | 0 | 0 | — | 0/4 |
| CFA + MBP | PBS | 2.0 | 0.7 | 15 | 5/7 |
| CFA + MBP + Example 2 | 10 mg/kg | 0.6 | 0.7 | 14 | 0/4 |
| CFA + MBP + Example 2 | 50 mg/kg | 0.8 | 0.6 | 15 | 0/4 |

Histologically, the Lewis rat EAE model typically shows perivascular and parenchymal inflammation due to an autoimmune myelin-specific T-cell response. Examination of histology specimens of the brain slices from animals subjected to Protocol 1 demonstrated that leukocyte migration across the blood-brain barrier had been completely prevented by the 50 mg/kg daily dosing schedule. There was no cuff formation and little CNS inflammation as a result.

The activity of Example 2 as a general inhibitor of inflammation was tested using the Mycobacterium footpad edema assay (MFE) in Wistar rats. Compound was administered daily by gavage at 2 mg/kg, 10 mg/kg, or 50 mg/kg.

Male outbred Wistar rats (110–125 g, Charles River Labs, Portage, Mich.) were used in this study. Rats were housed for a minimum of 1 week before use. Food and water were supplied ad libitum. Foot pad edema was induced following the method described by Martel R. R. and Klicius J., "Comparisons in rats of the anti-inflammatory and gastric irritant effects of etodolac with several clinically effective anti-inflammatory drugs", *Agents and Actions*, 1982;12:295. Briefly, male Wistar rats were injected subcutaneously into the right hind footpad with 0.1 mL of 5 mg/mL suspension of killed and dried *Mycobacterium butyricum* (Difco, Detroit, Mich.) in liquid paraffin. Compound was suspended in 0.5% hydroxypropylmethylcellulose (HPMC) containing 0.2% Tween-80 and administered orally 1 hour before injection. Subsequent doses of the compound were given 24 and 48 hours after the Mycobacterium. Control animals were given vehicle alone. Swelling was assessed on the third day by subtracting the initial volume (determined immediately following the Mycobacterium injection) from the final volume of the treated paw. Paw volume was determined by mercury plethysmography. The percent inhibition of edema achieved in each compound-treated group was determined by comparison with swelling in the vehicle-treated group and the $ID_{50}$ values were determined by regression analysis. Statistical significance between experimental groups was evaluated using a Student's t-test. Data is shown in Table IV. All the values for inhibition of the inflammatory response in this model were statistically significant.

TABLE IV

| Dose (mg/kg) | % Inhibition of Swelling |
|---|---|
| 2 | 23 |
| 10 | 27 |
| 50 | 40 |

Plasma concentrations of Example 2 peaked at 1 hour post-treatment and declined mono-exponentially through the subsequent 4 hours. Cmax and AUC(0–4) values increase proportionately with dose. Compound plasma concentrations determined from Cmax correspond to 4.62 μM (2-mg/kg dose), 38.8 μM (10-mg/kg dose), and 163 μM (50-mg/kg dose). The bioavailability of this compound is therefore well in excess of the effective range of gelatinase A and stromelysin-1 inhibition determined in the in vitro assays.

A compound of Formula Ia $$\text{Structure Ia}$$

wherein $$-\overset{O}{\underset{\|}{C}}-\underset{R}{\overset{}{CH}}-(CH_2)_a-\overset{O}{\underset{\|}{C}}-R^5$$

is attached at the 1 or 2 position of the A ring and $R$ and $R^a$ are each the same or different and each is hydrogen;

—$(CH_2)_n$-aryl wherein n is as defined above,

—$(CH_2)_n$-heteroaryl wherein n is as defined above,

—$(CH_2)_p$—$R^7$—$(CH_2)_q$-aryl wherein $R^7$ is O or S and p or q is each zero or an integer of 1 to 5 and the sum of p+q equals an integer of 5, —$(CH_2)_p$—$R^7$—$(CH_2)_q$-heteroaryl wherein p, q, and $R^7$ are as defined above, alkyl, —$(CH_2)_n$-cycloalkyl wherein n is as defined above, or —$(CH_2)_r$—$NH_2$ wherein r is an integer of 1 to 9;

a is zero or an integer of 1 to 3;

$R^5$ is OH, $OR^6$ wherein $R^6$ is as defined above, $$\underset{R^{6a}}{\overset{NR^6}{|}}$$

wherein $R^6$ and $R^{6a}$ are each the same or different and are as defined above for $R^6$, or NH—$OR^6$ wherein $R^6$ is as defined above;

$R^3$ and $R^4$ are each the same or different and each is hydrogen, alkyl, $NO_2$, halogen, $OR^6$ wherein $R^6$ is as defined above,

CN, $CO_2R^6$ wherein $R^6$ is as defined above, $SO_3R^6$ wherein $R^6$ is as defined above,

CHO, $$-\overset{O}{\underset{\|}{C}}-R$$

wherein R is as defined above, $$-\overset{O}{\underset{\|}{C}}-\underset{R^{6a}}{\overset{}{N}}-R^6$$

wherein $R^6$ and $R^{6a}$ are each the same or different and are as defined above for $R^6$, or $$-(CH_2)_n-\underset{R^{6a}}{\overset{}{N}}-R^6$$

wherein $R^6$ and $R^{6a}$ are each the same or different and are as defined above for $R^6$;

W, $W^1$, and $Z^1$ are each the same or different and each is $CR^3$ wherein $R^3$ is as defined above, or N providing only one of W or $W^1$ is N and/or only one of Z or $Z^1$ is N; and Y is $$-\underset{R}{N}-$$

wherein R is as defined above,

—O—,

—S—(O)$_m$— wherein m is zero or an integer of 1 or 2,

—CH$_2$—, $$-\underset{\underset{O}{\|}}{C}-,$$

$$-\underset{\underset{N-OR^6}{\|}}{C}-$$

wherein R$^6$ is as defined above, $$-\underset{OR^6}{CH}-$$

wherein R$^6$ is as defined above, $$-\underset{\underset{N-\underset{R^{6a}}{N}-R^6}{\|}}{C}-$$

wherein R$^6$ and R$^{6a}$ are the same or different and are as defined above for R$^6$, $$-\underset{\underset{O}{\|}}{C}-\underset{R^6}{N}-$$

wherein R$^6$ is as defined above, $$-\underset{R^6}{N}-\underset{\underset{O}{\|}}{C}-$$

wherein R$^6$ is as defined above, $$-\underset{\underset{O}{\|}}{C}-O-,$$

$$-O-\underset{\underset{O}{\|}}{C}-,$$

—CH$_2$—O—,

—O—CH$_2$—,

—CH$_2$—S(O)$_m$— wherein m is as defined above,

—S(O)$_m$—CH$_2$— wherein m is as defined above, $$-CH_2-\underset{R^6}{N}-$$

wherein R$^6$ is as defined above, $$-\underset{R^6}{N}-CH_2-$$

—CH=N—, or

—N=CH—;

wherein R$^6$ is as defined above, with the proviso that when R$^5$ is not NH—OR$^6$, at least one of R or R$^a$ is not hydrogen; and corresponding isomers thereof; or a pharmaceutically acceptable salt thereof may be prepared by reacting a compound of Formula II

II wherein M is Li or Mg-halogen, and is attached at the 1 or 2 position of the A ring, and R$^3$, R$^4$, Y, W, W$_1$, Z, and Z$^1$ are as defined above with a compound of Formula III

III wherein L is halogen,

—OR$^8$ wherein R$^8$ is methyl or ethyl, or $$-\underset{CH_3}{N}-OCH_3$$

and R, R$^a$, a and R$^5$ are as defined above using conventional methodology such as, for example, methodology disclosed by Nahm S. and Weinreb S. M., *Tetrahedron Letters*, 1981;22:3815 to afford a compound of Formula Ia.

A compound of Formula Ib

Ib wherein

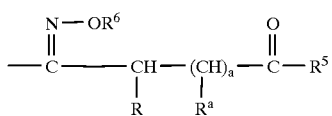

is attached at the 1 or 2 position of the A ring and

R$^6$ is hydrogen,

—(CH$_2$)$_n$-aryl wherein n is zero or an integer of 1 to 5, alkyl, or

—(CH$_2$)$_n$-cycloalkyl wherein n is as defined above; and R$^3$, R$^4$, Y, W, W$^1$, Z, Z$^1$, R, R$^a$, a, and R$^5$ are as defined above may be prepared by reacting a compound of Formula Ia with a compound of formula

wherein R$^6$ is as defined above using conventional methodology to afford a compound of Formula Ib.

A compound of Formula Ic

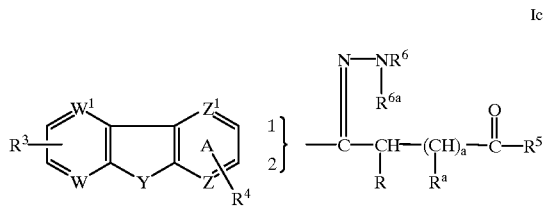

wherein

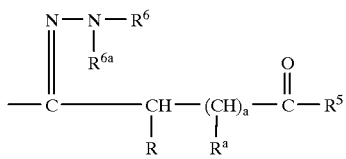

is attached at the 1 or 2 position of the A ring and R$^6$ and R$^{6a}$ are each the same or different and each is as defined above for R$^6$ and R$^3$, R$^4$, Y, W, W$^1$, Z, Z$^1$, R, R$^a$, a, and R$^5$ are as defined above may be prepared by reacting a compound of Formula I$_a$ with a compound of formula

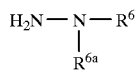

wherein R$^6$ and R$^{6a}$ are each the same or different and each is as defined above for R$^6$ using conventional methodology to afford a compound of Formula Ic.

Preferred synthetic routes are shown in Schemes 1 to 5 for preparing compounds of Formula I designated as Formulas Ia to Il.

Thus, in Scheme 1, a compound of Formula IV wherein R$^3$, R$^4$, W, W$^1$, Y, Z, and Z$^1$ are as defined above is acylated with a compound of Formula IIIa wherein L$^a$ is halogen, or

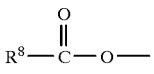

wherein R$^8$ is methyl or ethyl, and R, R$^a$, a, and R$^5$ are as defined above using conventional Friedel-Craft (F-C) conditions. For example, a compound of Formula IV is reacted with an acid chloride or anhydride of a compound of Formula IIIa either neat or in an inert solvent such as, for example, dichloromethane, 1,2-dichloroethane, and the like in the presence of a Lewis acid such as FeCl$_3$, AlCl$_3$, ZnCl$_2$, and the like at about −30° C. to about 150° C. to afford a compound of Formula Ia wherein the moiety

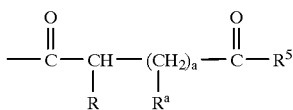

is attached at the 1 or 2 position of the A ring.

It is understood that the regiochemistry of the products from the F-C acylation depend upon the electronics of the aromatic ring system and so, only certain regioisomers of Formula Ia will be directly accessible utilizing this route. For example, F-C acylation will yield the following regioisomers: 2-dibenzofuranyl, 2-dibenzothiophenyl, 3-dibenzo-5,5-dioxo-thiophenyl, 2-fluorenyl, and the like when the rings are unsubstituted.

When the two terminal rings of the linear tricyclic heterocycle are different, the regioselectivity of the F-C will favor the more electron-rich ring system. Thus, decreasing the electron density of a ring (i.e., by nitration or halogenation) will increase the acylation in the other ring system. On the other hand, increasing the electron density (with substituents such as alkoxy) will tend to favor F-C acylation in the affected ring.

Compounds of Formula Ib and Formula Ic are prepared from a compound of Formula Ia using the methodology previously described for converting a compound of Formula Ia to a compound of Formula Ib or a compound of Formula Ia to a compound of Formula Ic.

Scheme 2 discloses an alternate route to preparing compounds of Formula I. Thus, a compound of Formula V wherein the aldehyde moiety (CHO) is attached to the 1 or 2 position of the A ring and R$^3$, R$^4$, W, W$^1$, Y, Z, and Z$^1$ are as defined above is reacted with an acrylate of Formula VI wherein R, R$^a$, and R$^5$ are as defined above using conventional methodology to afford a compound of Formula Id wherein the moiety

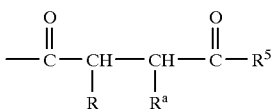

is attached at the 1 or 2 position of the A ring and R$^3$, R$^4$, W, W$^1$, Y, Z, Z$^1$, R, R$^a$, and R$^5$ are as defined above.

Compounds of Formula Ie and Formula If are prepared from a compound of Formula Id using the methodology previously described for converting a compound of Formula Ia to a compound of Formula Ib and a compound of Formula Ia to a compound of Formula Ic.

Schemes 3 and 4 disclose procedures for preparing specific regioisomers of a compound of Formula I. Thus, a compound of Formula VII or Formula VIIa wherein R$^3$, W, and $W^1$ are as defined above is reacted with phosphorous oxychloride in dimethylformamide to afford a compound of Formula VIII or Formula VIIIa, respectively, wherein $R^3$, W, and $W^1$ are as defined above. A compound of Formula VIII or Formula VIIIa is reacted with a compound of Formula IX wherein R, $R^a$, and $R^5$ are as defined above using methodology previously described for converting a compound of Formula V into a compound of Formula Id to afford a compound of Formula Ig or a compound of Formula Ij.

Compounds of Formula Ih, Formula Ii, Formula Ik, and Formula Il are prepared, respectively, from a compound of Formula Ig or Formula Ij using methodology previously described for converting a compound of Formula Ia to a compound of Formula Ib or a compound of Formula Ia to a compound of Formula Ic.

Scheme 5 discloses a procedure for preparing optically active side chains of Formula XVI which can be used to prepare optically active compounds of Formula I. Thus, R or S 4-benzyl-2-oxazolidinone (Formula X) is reacted with an acid chloride of Formula XI wherein R is as defined above to afford a compound of Formula XII wherein R is as defined above.

A compound of Formula XII is reacted with a compound of Formula XIII wherein $R^a$ is as defined above in the presence of KHMDS to afford a compound of Formula XIV wherein R and $R^a$ are as defined above. The diastereomers of a compound of Formula XIV are separated followed by reaction with $LiOH/H_2O_2$ and subsequent reaction with oxalyl chloride to afford a compound of Formula XV wherein R and $R^a$ are as defined above. A compound of Formula XV is reacted with N,O-dimethylhydroxylamine hydrochloride in the presence of pyridine to afford a compound of Formula XVI wherein R and $R^a$ are as defined above.

Compounds of Formulas II, III, IIIa, IV, V, VI, VII, VIIa, IX, X, XI, and XIII are either known or can be prepared by methods known in the art.

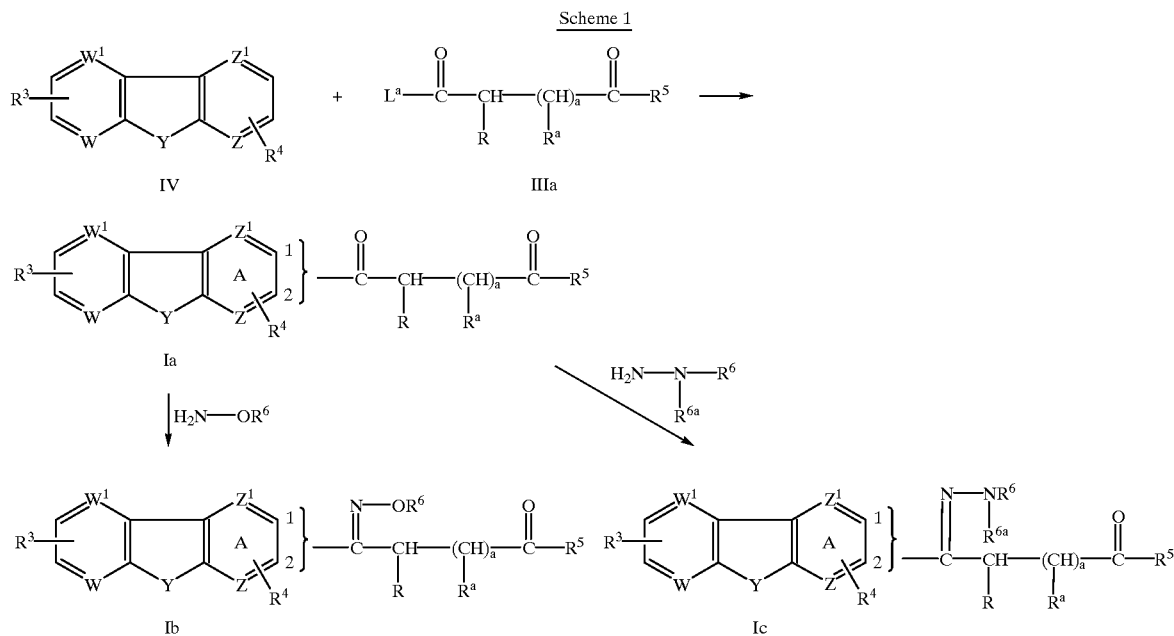

Scheme 1

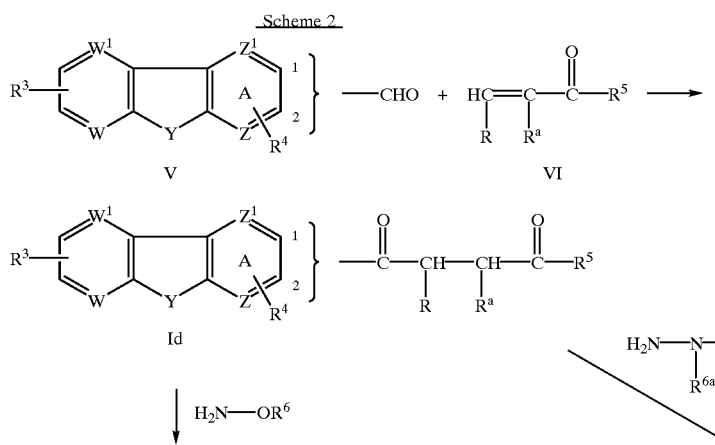

Scheme 2

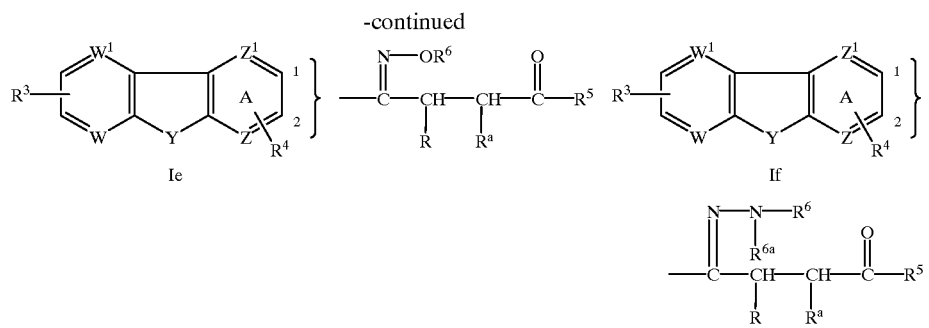
Scheme 3
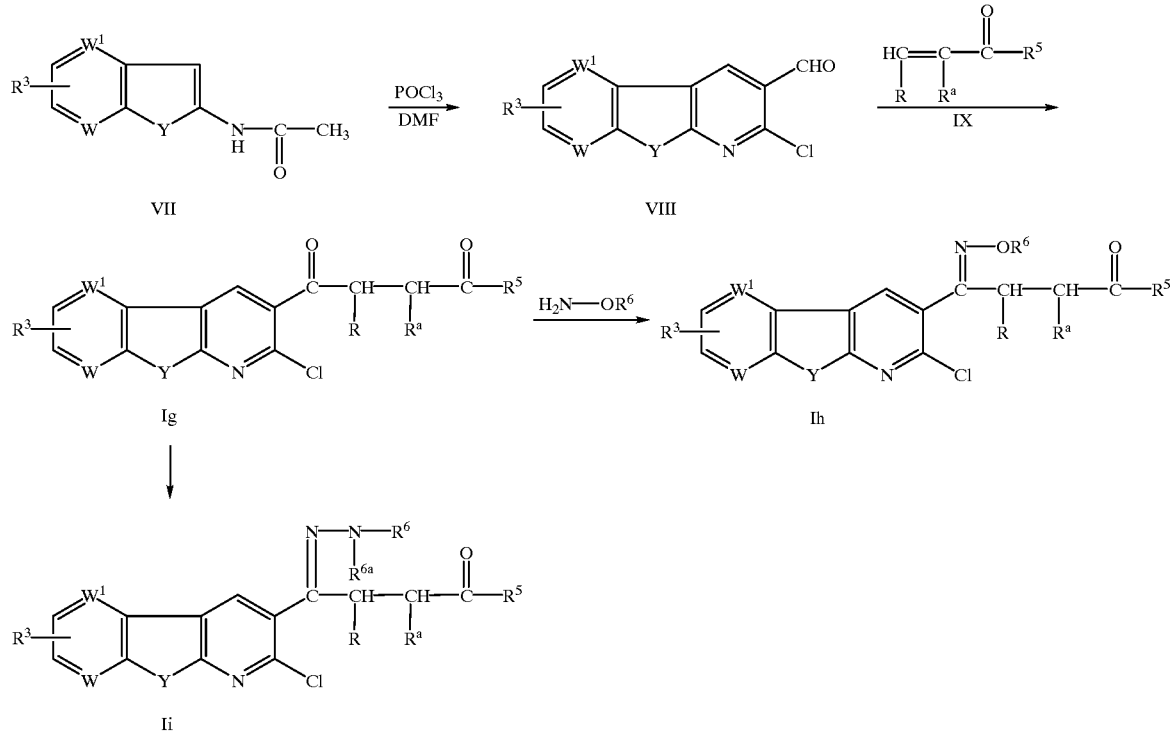
Scheme 4
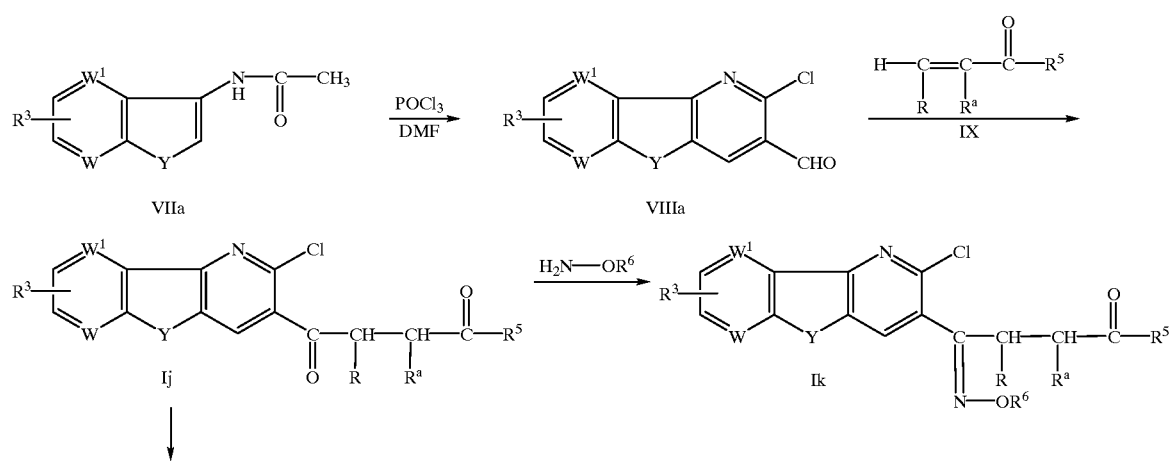

-continued

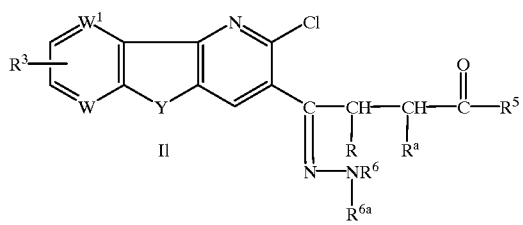

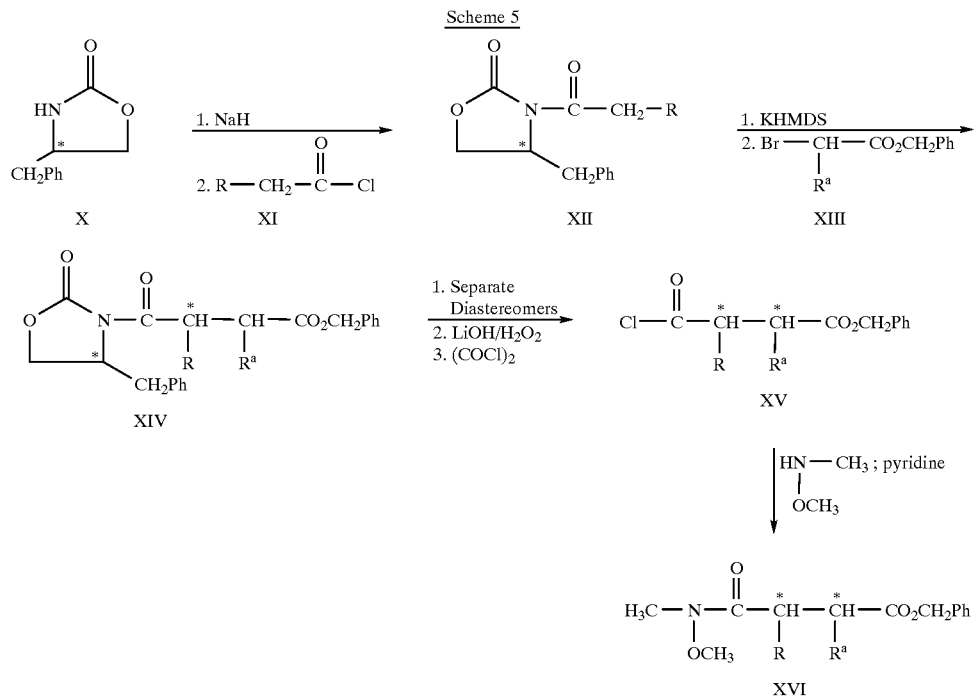

* designates R or S

The compounds of the present invention can be prepared and administered in a wide variety of oral and parenteral dosage forms. Thus, the compounds of the present invention can be administered by injection, that is, intravenously, intramuscularly, intracutaneously, subcutaneously, intraduodenally, or intraperitoneally. Also, the compounds of the present invention can be administered by inhalation, for example, intranasally. Additionally, the compounds of the present invention can be administered transdermally. It will be obvious to those skilled in the art that the following dosage forms may comprise as the active component, either a compound of Formula I or a corresponding pharmaceutically acceptable salt of a compound of Formula I.

For preparing pharmaceutical compositions from the compounds of the present invention, pharmaceutically acceptable carriers can be either solid or liquid. Solid form preparations include powders, tablets, pills, capsules, cachets, suppositories, and dispersible granules. A solid carrier can be one or more substances which may also act as diluents, flavoring agents, solubilizers, lubricants, suspending agents, binders, preservatives, tablet disintegrating agents, or an encapsulating material.

In powders, the carrier is a finely divided solid which is in a mixture with the finely divided active component.

In tablets, the active component is mixed with the carrier having the necessary binding properties in suitable proportions and compacted in the shape and size desired.

The powders and tablets preferably contain from five or ten to about seventy percent of the active compound. Suitable carriers are magnesium carbonate, magnesium stearate, talc, sugar, lactose, pectin, dextrin, starch, gelatin, tragacanth, methylcellulose, sodium carboxymethylcellulose, a low melting wax, cocoa butter, and the like. The term "preparation" is intended to include the formulation of the active compound with encapsulating material as a carrier providing a capsule in which the active component, with or without other carriers, is surrounded by a carrier, which is thus in association with it. Similarly, cachets and lozenges are included. Tablets, powders, capsules, pills, cachets, and lozenges can be used as solid dosage forms suitable for oral administration.

For preparing suppositories, a low melting wax, such as a mixture of fatty acid glycerides or cocoa butter, is first melted and the active component is dispersed homogeneously therein, as by stirring. The molten homogenous mixture is then poured into convenient sized molds, allowed to cool, and thereby to solidify.

Liquid form preparations include solutions, suspensions, and emulsions, for example, water or water propylene glycol solutions. For parenteral injection, liquid preparations can be formulated in solution in aqueous polyethylene glycol solution.

Aqueous solutions suitable for oral use can be prepared by dissolving the active component in water and adding suitable colorants, flavors, stabilizing, and thickening agents as desired.

Aqueous suspensions suitable for oral use can be made by dispersing the finely divided active component in water with viscous material, such as natural or synthetic gums, resins, methylcellulose, sodium carboxymethylcellulose, and other well-known suspending agents.

Also included are solid form preparations which are intended to be converted, shortly before use, to liquid form preparations for oral administration. Such liquid forms include solutions, suspensions, and emulsions. These preparations may contain, in addition to the active component, colorants, flavors, stabilizers, buffers, artificial and natural sweeteners, dispersants, thickeners, solubilizing agents, and the like.

The pharmaceutical preparation is preferably in unit dosage form. In such form, the preparation is subdivided into unit doses containing appropriate quantities of the active component. The unit dosage form can be a packaged preparation, the package containing discrete quantities of preparation, such as packeted tablets, capsules, and powders in vials or ampoules. Also, the unit dosage form can be a capsule, tablet, cachet, or lozenge itself, or it can be the appropriate number of any of these in packaged form.

The quantity of active component in a unit dose preparation may be varied or adjusted from 1 mg to 1000 mg, preferably 10 mg to 100 mg according to the particular application and the potency of the active component. The composition can, if desired, also contain other compatible therapeutic agents.

In therapeutic use as agents for the treatment of multiple sclerosis, atherosclerotic plaque rupture, aortic aneurism, heart failure, restenosis, periodontal disease, corneal ulceration, cancer metastasis, tumor angiogenesis, arthritis, or other autoimmune or inflammatory disorders dependent upon tissue invasion by leukocytes, the compounds utilized in the pharmaceutical method of this invention are administered at the initial dosage of about 1 mg to about 100 mg per kilogram daily. A daily dose range of about 25 mg to about 75 mg per kilogram is preferred. The dosages, however, may be varied depending upon the requirements of the patient, the severity of the condition being treated, and the compound being employed. Determination of the proper dosage for a particular situation is within the skill of the art. Generally, treatment is initiated with smaller dosages which are less than the optimum dose of the compound. Thereafter, the dosage is increased by small increments until the optimum effect under the circumstance is reached. For convenience, the total daily dosage may be divided and administered in portions during the day if desired.

The following nonlimiting examples illustrate the inventors' preferred methods for preparing the compounds of the invention.

EXAMPLE 1
γ-Oxo-2-dibenzofuranbutanoic acid

A 5-L, three-necked, round-bottom flask is equipped with a mechanical stirrer, thermocouple thermometer, and a powder funnel with a nitrogen inlet. This flask is charged with 1.5 L of dichloromethane, flushed with nitrogen and aluminum chloride (196 g, 1.44 mol) is added portionwise. The resulting slurry is cooled in a dry ice bath while a dry powdered mixture of dibenzofuran (100 g, 0.595 mol) and succinic anhydride (71.5 g, 0.714 mol) is added portionwise. Addition is at a rate sufficient to keep the reaction temperature less than −30° C. and is completed in 15 minutes. The resulting mixture is stirred at this temperature for 2 hours then slowly treated with aqueous HCl (375 mL of conc. HCl in 1 L of solution). During addition of the HCl solution, the temperature is controlled to a maximum of 3° C. and addition is completed in 45 minutes. The dichloromethane is then removed in vacuo, the aqueous slurry is filtered, and the solid is air dried to give 175 g of white solid. This solid is extracted into 4 L of tetrahydrofuran (THF), treated with Darco, and filtered. The filtrate was evaporated leaving a cream-colored solid which was recrystallized from 95% ethanol to give 180 g of crude product. This solid is recrystallized from toluene (10 L in 4 portions), and the solids are washed with hexanes then dried in vacuo to give 119.5 g (mp 186–188° C., 75% yield) of the title compound.

EXAMPLE 2
4-Dibenzofuran-2-yl-4-hydroximino-butyric acid

A solution of γ-oxo-2-dibenzofuranbutanoic acid (Example 1) (75.5 g) and sodium acetate trihydrate (114.9 g) in methanol (2.5 L) is treated with a solution of hydroxylamine hydrochloride (38.9 g) in water (150 mL of solution). The solution is heated to reflux for 3.5 hours then concentrated, cooled, and filtered. This solid was washed with water then dried in vacuo to give the crude title compound (71.32 g, 89.6% of theory). This solid was recrystallized from ethyl acetate, washed with hexane, and dried in vacuo to give 53.04 g (68% yield) of the title compound; mp 167–168° C. (d).

We claim:
1. A compound of Formula I

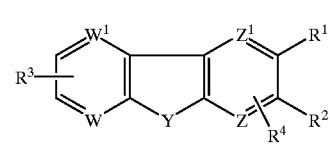

wherein one of $R^1$ or $R^2$ is

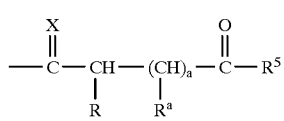

wherein X is O,

N—$OR^6$ wherein $R^6$ is hydrogen,
—$(CH_2)_n$-aryl wherein n is zero or an integer of 1 to 5, alkyl, or
—$(CH_2)_n$-cycloalkyl wherein n is as defined above, or

wherein $R^6$ and $R^{6a}$ are each the same or different and each is as defined above for $R^6$;

R and $R^a$ are each the same or different and each is hydrogen,
—$(CH_2)_n$-aryl wherein n is as defined above,
—$(CH_2)_n$-heteroaryl wherein n is as defined above,
—$(CH_2)_p$—$R^7$—$(CH_2)_q$-aryl wherein $R^7$ is O or S and p or q is each zero or an integer of 1 to 5 and the sum of p+q equals an integer of 5, —$(CH_2)_p$—$R^7$—$(CH_2)_q$-heteroaryl wherein p, q, and $R^7$ are as defined above,
alkyl,
—$(CH_2)_n$-cycloalkyl wherein n is as defined above, or
—$(CH_2)_r$—$NH_2$ wherein r is an integer of 1 to 9;
a is zero or an integer of 1 to 3;
$R^5$ is OH,
  $OR^6$ wherein $R^6$ is as defined above,

wherein $R^6$ and $R^{6a}$ are each the same or different and are as defined above for $R^6$, or
NH—$OR^6$ wherein $R^6$ is as defined above;
$R^3$ and $R^4$ are each the same or different and each is
hydrogen,
alkyl,
$NO_2$,
halogen,
$OR^6$ wherein $R^6$ is as defined above,
CN,
$CO_2R^6$ wherein $R^6$ is as defined above,
$SO_3R^6$ wherein $R^6$ is as defined above,
CHO,

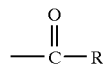

wherein R is as defined above,

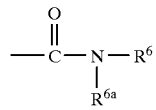

wherein $R^6$ and $R^{6a}$ are each the same or different and are as defined above for $R^6$, or

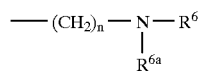

wherein $R^6$ and $R^{6a}$ are each the same or different and are as defined above for $R^6$;
W, $W^1$, Z, and $Z^1$ are each the same or different and each is $CR^3$ wherein $R^3$ is as defined above, or
N providing only one of W or $W^1$ is
N and/or only one of Z or $Z^1$ is N; and
Y is

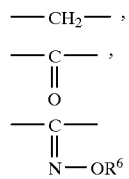

wherein $R^6$ is as defined above,

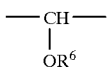

wherein $R^6$ is as defined above or

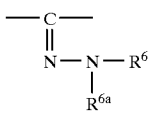

wherein $R^6$ and $R^{6a}$ are the same or different and are as defined above for $R^6$
with the proviso that when X is O, and $R^5$ is not NH—$OR^6$, at least one of R or $R^a$ is not hydrogen and with the further proviso that when $R^3$ and $R^4$ are hydrogen: W; $W^1$ Z and $Z^1$ are each CH; and Y is —$CH_2$— then $R^1$ or $R^2$ is not

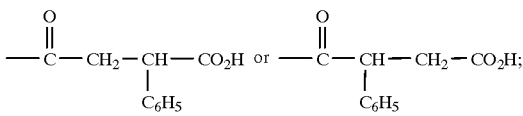

and corresponding isomers thereof; or a pharmaceutically acceptable salt thereof.

2. A compound according to claim 1 wherein W, $W^1$, Z, and $Z^1$ are $CR^3$; and corresponding isomers thereof; or a pharmaceutically acceptable salt thereof.

3. A compound according to claim 2 wherein
Y is

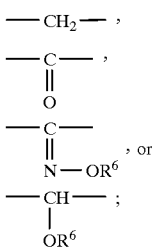

and corresponding isomers thereof;
or a pharmaceutically acceptable salt thereof.

4. A compound according to claim 3 wherein one of R or $R^a$ is other than hydrogen; and corresponding isomers thereof; or a pharmaceutically acceptable salt thereof.

5. A compound according to claim 3 wherein X is N—$OR^6$; and corresponding isomers thereof; or a pharmaceutically acceptable salt thereof.

6. A compound according to claim 5 wherein $R^5$ is OH; and corresponding isomers thereof, or a pharmaceutically acceptable salt thereof.

7. A compound according to claim 2 wherein X is O and $R^5$ is NH—$OR^6$; and corresponding isomers thereof; or a pharmaceutically acceptable salt thereof.

8. A compound according to claim 1 wherein W, $W^1$, Z and $Z^1$ is N providing only one of W or $W^1$ is N and/or only one of Z or $Z^1$ is N; and corresponding isomers thereof; or a pharmaceutically acceptable salt thereof.

9. A compound according to claim 8 wherein R or $R_a$ is other than hydrogen; and corresponding isomers thereof; or a pharmaceutically acceptable salt thereof.

10. A compound according to claim 8 wherein X is N—OR$^6$; and corresponding isomers thereof; or a pharmaceutically acceptable salt thereof.

11. A compound according to claim 10 wherein R$^5$ is OH; and corresponding isomers thereof; or a pharmaceutically acceptable salt thereof.

12. A compound according to claim 8 wherein X is O and R$^5$ is NH—OR$^6$; and corresponding isomers thereof; or a pharmaceutically acceptable salt thereof.

13. A method of inhibiting a matrix metalloproteinase comprising administering to a host suffering therefrom a therapeutically effective amount of a compound according to claim 1 in unit dosage form.

14. A pharmaceutical composition comprising a compound according to claim 1 in admixture with a pharmaceutically acceptable excipient, diluent, or carrier.

15. A pharmaceutical composition adapted for administration as an agent for treating atherosclerotic plaque rupture, aortic aneurism, heart failure, restenosis, periodontal disease, corneal ulceration, cancer metastasis, arthritis, and autoimmune or inflammatory diseases dependent upon tissue invasion by leukocytes comprising a therapeutically effective amount of a compound according to claim 1 in admixture with a pharmaceutically acceptable excipient, diluent, or carrier.

16. A pharmaceutical composition adapted for administration as an agent for treating multiple sclerosis comprising a therapeutically effective amount of a compound according to claim 1 in admixture with a pharmaceutically acceptable excipient, diluent, or carrier.

* * * * *